(12) United States Patent
Patangay et al.

(10) Patent No.: US 8,360,983 B2
(45) Date of Patent: Jan. 29, 2013

(54) APNEA TYPE DETERMINING APPARATUS AND METHOD

(75) Inventors: Abhilash Patangay, Inver Grove Heights, MN (US); Yachuan Pu, Laguna Niguel, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 23 days.

(21) Appl. No.: 13/172,332

(22) Filed: Jun. 29, 2011

(65) Prior Publication Data

US 2012/0029362 A1 Feb. 2, 2012

Related U.S. Application Data

(63) Continuation-in-part of application No. 12/700,942, filed on Feb. 5, 2010, now Pat. No. 7,976,470, which is a continuation of application No. 11/425,820, filed on Jun. 22, 2006, now Pat. No. 7,678,058.

(51) Int. Cl.
*A61B 5/08* (2006.01)
(52) U.S. Cl. ......... 600/484; 600/485; 600/486; 600/529
(58) Field of Classification Search .................. 600/484, 600/485, 506, 529
See application file for complete search history.

(56) References Cited

U.S. PATENT DOCUMENTS

| | | | |
|---|---|---|---|
| 4,129,125 A | 12/1978 | Lester et al. |
| 4,648,407 A | 3/1987 | Sackner |
| 4,777,962 A | 10/1988 | Watson et al. |
| 5,146,918 A | 9/1992 | Kallok et al. |
| 5,174,287 A | 12/1992 | Kallok et al. |
| 5,215,082 A | 6/1993 | Kallok et al. |
| 5,275,159 A | 1/1994 | Griebel |
| 5,368,040 A | 11/1994 | Carney |
| 5,385,144 A | 1/1995 | Yamanishi et al. |
| 5,458,137 A | 10/1995 | Axe et al. |
| 5,935,081 A | 8/1999 | Kadhiresan |
| 5,974,340 A | 10/1999 | Kadhiresan |
| 6,064,910 A | 5/2000 | Andersson et al. |
| 6,076,015 A | 6/2000 | Hartley et al. |
| 6,126,611 A | 10/2000 | Bourgeois et al. |
| 6,208,900 B1 | 3/2001 | Ecker et al. |
| 6,368,283 B1 | 4/2002 | Xu et al. |
| 6,527,729 B1 | 3/2003 | Turcott |
| 6,641,542 B2 | 11/2003 | Cho et al. |
| 6,856,829 B2 | 2/2005 | Ohsaki et al. |
| 6,865,419 B2 | 3/2005 | Mulligan et al. |
| 6,869,404 B2 | 3/2005 | Schulhauser et al. |
| 6,887,207 B2 | 5/2005 | Hettrick |
| 6,918,878 B2 | 7/2005 | Brodnick |
| 7,225,021 B1 | 5/2007 | Park et al. |

(Continued)

FOREIGN PATENT DOCUMENTS

EP 1488743 A2 12/2004
EP 1551286 A2 7/2005

OTHER PUBLICATIONS

"U.S. Appl. No. 11/425,820, Non-Final Office Action mailed Feb. 18, 2009", 13 pgs.

(Continued)

*Primary Examiner* — Patricia Mallari
*Assistant Examiner* — Michael D'Angelo
(74) *Attorney, Agent, or Firm* — Schwegman Lundberg & Woessner, P.A.

(57) ABSTRACT

An apnea classification system provides for apnea monitoring and differentiation based on several sleep apnea related parameters for diagnostic and therapeutic purposes. Monitoring of such sleep apnea related parameters allows the apnea classification system to differentiate among the different types of apnea and hypopnea and to identify an occurrence of periodic respiration. This information may then be used to determine the best method of therapy, or adjust current therapy parameters to more effectively treat a subject.

20 Claims, 9 Drawing Sheets

U.S. PATENT DOCUMENTS

| | | |
|---|---|---|
| 7,510,531 B2 | 3/2009 | Lee et al. |
| 7,678,058 B2 | 3/2010 | Patangay et al. |
| 7,976,470 B2 | 7/2011 | Patangay et al. |
| 2002/0029000 A1 | 3/2002 | Ohsaki et al. |
| 2002/0185130 A1 | 12/2002 | Wright et al. |
| 2004/0134496 A1 | 7/2004 | Cho et al. |
| 2005/0217674 A1 | 10/2005 | Burton et al. |
| 2005/0222502 A1 | 10/2005 | Cooper |
| 2005/0261600 A1 | 11/2005 | Aylsworth |
| 2007/0142727 A1 | 6/2007 | Zhang et al. |
| 2008/0009755 A1 | 1/2008 | Patangay et al. |
| 2010/0137723 A1 | 6/2010 | Patangay et al. |

OTHER PUBLICATIONS

"U.S. Appl. No. 11/425,820, Notice of Allowance mailed Oct. 30, 2009", 6 pgs.

"U.S. Appl. No. 11/425,820, Response filed Jun. 18, 2009 to Non Final Office Action mailed Feb. 18, 2009", 13 pgs.

"U.S. Appl. No. 12/700,942 Non-Final Office Action mailed Sep. 8, 2010", 7 pgs.

"U.S. Appl. No. 12/700,942, Notice of Allowance mailed Mar. 4, 2011", 7 pgs.

"U.S. Appl. No. 12/700,942, Response filed Dec. 8, 2010 to Non Final Office Action mailed Sep. 8, 2010", 10 pgs.

Brooks, D., et al., "Obstructive Sleep Apnea as a Cause of Systemic Hypertension", J Clin Invest., 99(1), (Jan. 1, 1997), 106-9.

Chen, L., et al., "Hemodynamic effects of periodic obstructive apneas in sedated pigs with congestive heart failure", J Appl Physiol., 88(3), (Mar. 2000), 1051-60.

Chen, L., et al., "Systemic and myocardial hemodynamics during periodic obstructive apneas in sedated pigs", J Appl Physiol., 84(4), (Apr. 1998), 1289-98.

Parker, J. D., et al., "Acute and chronic effects of airway obstruction on canine left ventricular performance", Am J Respir Crit Care Med., 160(6), (Dec. 1999), 1888-96.

Schneider, H., et al., "Effects of arousal and sleep state on systemic and pulmonary hemodynamics in obstructive apnea", Journal of Applied Physiology, 88(3), (Mar. 2000), 1084-1092.

Schneider, H., et al., "Systemic and pulmonary hemodynamic responses to normal and obstructed breathing during sleep", J Appl Physiol., 83(5), (Nov. 1997), 1671-80.

Tilkian, A. G., et al., "Hemodynamics in sleep-induced apnea. Studies during wakefulness and sleep.", Ann Intern Med., 85(6), (Dec. 1976), 714-9.

Tkacova, R., et al., "Effects of continuous positive airway pressure on obstructive sleep apnea and left ventricular afterload in patients with heart failure", Circulation., 98(21), (Nov. 24, 1998), 2269-75.

Virolainen, J., et al., "Effect of negative intrathoracic pressure on left ventricular pressure dynamics and relaxation", J Appl Physiol., 79(2), (Aug. 1995), 455-60.

APNEA TYPE DETERMINING APPARATUS AND METHOD

CROSS REFERENCE TO RELATED APPLICATIONS

This application is a Continuation-in-Part of U.S. application Ser. No. 12/700,942, filed on Feb. 5, 2010, which is a continuation of U.S. application Ser. No. 11/425,820, filed on Jun. 22, 2006, now issued as U.S. Pat. No. 7,678,058, each of which is incorporated herein by reference, and the benefit of priority of each of which is claimed herein.

TECHNICAL FIELD

This patent document pertains generally to implantable medical devices, and more particularly, but not by way of limitation, to a method and apparatus for determining the type of sleep apnea in a patient.

BACKGROUND

Sleep apnea involves a brief cessation of breathing during sleep. There exist two types of sleep apnea: central sleep apnea ("CSA"), which is associated with the failure of the body to automatically initiate and control a respiratory cycle at the proper time; and obstructive sleep apnea ("OSA"), which is associated with a blockage of the airway.

The most common type of sleep apnea is central sleep apnea. Central sleep apnea typically causes cessation of substantially all respiratory effort during sleep. This condition may be developed after a heart attack, and is usually a contributing factor to heart failure and other cardiopulmonary disorders.

The other type of sleep apnea is obstructive sleep apnea. Obstructive sleep apnea is generally characterized by repetitive pauses in breathing during sleep due to upper airway obstruction or collapse and is commonly found in overweight people who snore or have oversized necks. When awake, muscle tone keeps the throat open. When asleep, the airway of the neck narrows and closes. The person struggles to breathe against the collapsed throat as if choking. As the patient wakes up, the muscles of the throat open the airway. Many patients with congestive heart failure ("CHF") suffer from obstructive sleep apnea.

Heart condition is typically worsened by excessive stress during apnea. Thus, the detection of sleep apnea is important.

Sleep apnea, once diagnosed in a patient, may be treated through several methods, including continuous positive airway pressure ("CPAP"), and electrical stimulation of the heart, diaphragm, or upper airway muscles.

Presently, sleep apnea detection is accomplished by several methods, including the detection of respiration, such as by monitoring the transthoracic impedance and other techniques.

SUMMARY

When detecting sleep apnea through respiration, it is difficult to differentiate between the different types of sleep apnea, mainly obstructed sleep apnea and central sleep apnea. This document describes an improved method and apparatus for detecting and determining the type of sleep apnea in a patient.

An apnea classification system provides for apnea monitoring and differentiation based on several sleep apnea related parameters for diagnostic and therapeutic purposes. Monitoring of such sleep apnea related parameters allows the apnea classification system to differentiate among the different types of apnea. This information may then be used to determine the best method of therapy, or adjust current therapy parameters to more effectively treat a subject.

In one example, a system includes multiple apnea detectors and an apnea classification module. A first apnea detector is respiration-based and is indicative of a general apnea event, or a cessation of breathing for a period of time. A second apnea detector is non-respiration-based and is indicative of a specific type of apnea. The apnea classification module receives data from both sensors and differentiates between the different types of apnea, namely obstructive sleep apnea and central sleep apnea. Therapy can then be implemented based upon the type of apnea determined.

The respiration-based apnea detector may be implemented in several ways. In one example, the respiration-based apnea detector comprises of at least one of a respiration sensor, an impedance sensor, a pressure sensor, an accelerometer, a heart sound sensor, an acoustic sensor, a position sensor, or a thermister.

The non-respiration-based apnea detector may be implemented in several ways. In one example, the non-respiration-based apnea detector comprises of at least one of a pressure sensor and a heart sound sensor, in which the pressure sensor comprises of at least one of a pulmonary artery pressure sensor and a left ventricle pressure sensor, and the heart sound sensor comprises of at least one of an acoustic sensor, an accelerometer, a position sensor, or an activity sensor.

In another example, a method includes sensing a respiration signal, detecting at least one of a blood pressure signal and a heart sound signal, detecting an apnea event from at least one of a respiration signal, a blood pressure signal, and a heart sound signal, and distinguishing between obstructive sleep apnea and central sleep apnea using information from the respiration signal and information from at least one of the blood pressure signal and the heart sound signal. Therapy can then be implemented based on the type of apnea determined.

A respiration signal may be sensed in several ways. In one example, sensing the respiration signal comprises of at least one of sensing a thoracic impedance, extracting respiration information from a blood pressure signal, extracting respiration information from an acceleration, extracting respiration information from heart sounds, extracting respiration information from an acoustic sensor, extracting respiration information from a temperature.

A blood pressure signal may be detected in several ways. In one example, detecting a blood pressure signal comprises at least one of sensing pulmonary artery blood pressure and sensing left ventricle blood pressure.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

As a person is experiencing obstructive sleep apnea, certain indicators are present that are absent during a central sleep apnea event. Certain other indicators are present during a central sleep apnea event that are absent during an obstructive sleep apnea event. Other indicators are present during both types of events. Thus, by collecting multiple indicators of sleep apnea and comparing their results, the type of sleep apnea can better be determined.

Figure 1:
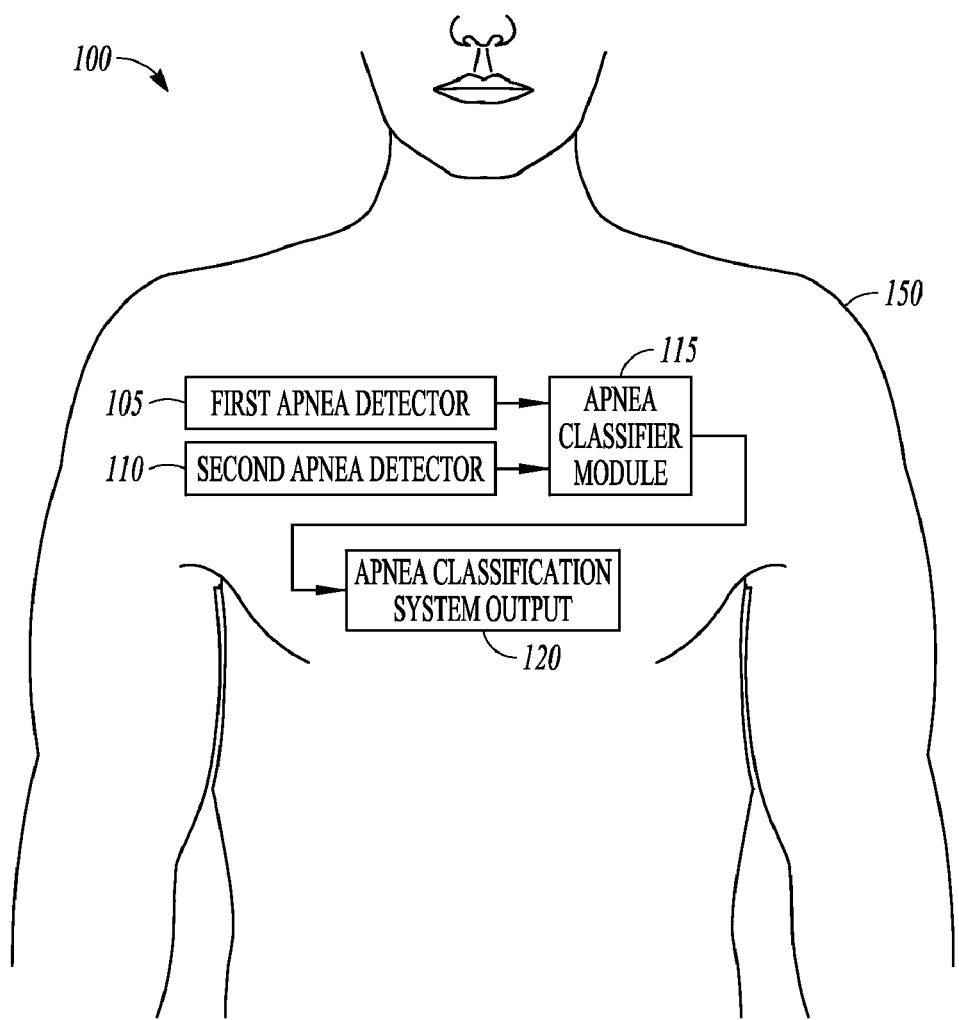
FIG. 1 is a schematic/block diagram illustrating generally the basic apparatus components according to one example.

FIG. 1 is a schematic/block diagram illustrating generally, by way of example, but not by way of limitation, one example of the basic apparatus components of an apnea classification system 100. System 100 includes, among other things, an apnea classifier module 115 for receiving data from a first implantable or external apnea detector 105 and a second implantable or external apnea detector 110.

First apnea detector 105 is respiration-based, and typically includes a respiration sensor. A respiration-based apnea detector senses, either directly or indirectly, whether the subject is breathing to detect apnea. The respiration-based apnea detector produces a sensor signal that includes cyclic variations indicative of inhaling and exhaling. For example, a thoracic impedance sensor includes cyclic variations as the subject inhales or exhales. In certain other examples, blood pressure and heart sound signals include components that are indicative of cyclic variations as the subject inhales or exhales. When so configured, a blood pressure sensor or a heart sound sensor may also be considered a respiration-based apnea detector.

Second apnea detector 110 is non-respiration-based, and typically includes at least one of a blood pressure sensor or a heart sound sensor. A non-respiration-based apnea detector senses, either directly or indirectly, a parameter indicative of apnea other than whether the subject is breathing. For example, certain other components of blood pressure and heart sound signals do not include the cyclic variations resulting from inhaling and exhaling. However, such other components of blood pressure and heart sound signals may have other information relevant to whether apnea is present or whether a type of apnea is present, as discussed below. As an illustrative first example of such a non-respiration indicator of apnea, there may be a change in left ventricle end diastolic pressure (LVEDP) during inspiratory efforts against a closed airway. Because the airway is closed, there is generally no cyclic variation in the pressure signal arising from inhaling or exhaling. However, during such an apnea episode, the LVEDP tends to gradually change over a time period that would correspond to several respiratory cycles, if such respiratory cycles were present. See, e.g., from 210 to 215 in FIG. 2, discussed below. Although such a change is affected by respiration, since it does not manifest cyclic information corresponding to inhaling and exhaling cycles, it is not considered to be a respiration sensor within the meaning of this document. As an illustrative second example, there may be gradual rise in S1 heart sound amplitude during obstructed breathing. See, e.g., from 325 to 330 in FIG. 3, as discussed below. Although heart sound information can be used to extract cyclic variations resulting from inhaling and exhaling, the gradual rise in S1 heart sound amplitude during obstructed breathing does not provide such cyclic variations from inhaling and exhaling. Thus, this component of the heart sound signal is not considered to be a respiration sensor within the meaning of this document.

Apnea classifier module 115 receives information from first apnea detector 105 and second apnea detector 110, and provides a resulting apnea classification at apnea classification system output 120.

In one example, apnea classifier module 115 receives data from first apnea detector 105 and second apnea detector 110. Using information from each, the apnea classifier module determines the type of apnea present within the subject, and outputs the resulting apnea classification at apnea classification system output 120.

Figure 1A:
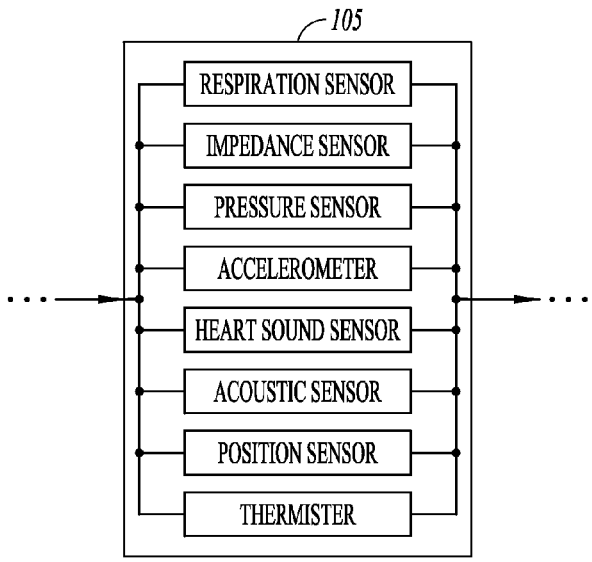
FIG. 1A is a schematic/block diagram illustrating apnea detector components according to one example.

FIG. 1A is a schematic/block diagram illustrating generally, by way of example, but not by way of limitation, one example of implementing first apnea detector 105 of apnea classification system 100. First apnea detector 105 typically includes a respiration sensor, such as a thoracic or intracardiac impedance-based respiration sensor, a blood pressure based respiration sensor, and accelerometer based respiration sensor, a heart sound sensor for respiration sensing, a position sensor for determining respiration, or a thermister for sensing respiration.

Figure 2:
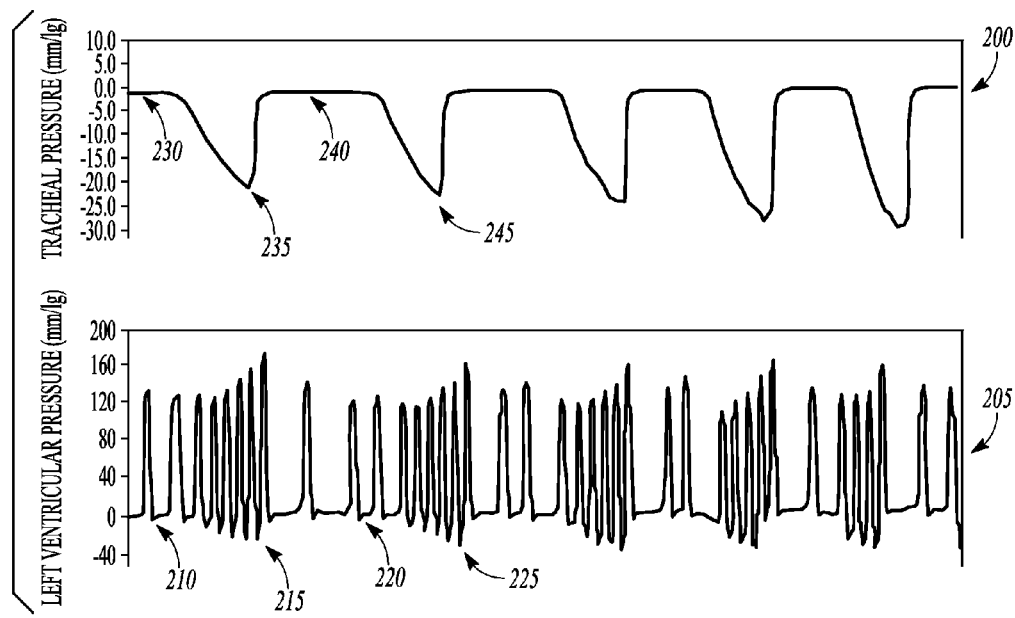
FIG. 2 is a graphical illustration of tracheal pressure and absolute left ventricular pressure during a series of inspiratory efforts against a closed airway.

In one example, respiration is detected by a respiration sensor placed over the mouth, the nasal openings, or both. In another example, respiration is detected by a transthoracic impedance sensor, as illustrated in FIG. 2. In another example, respiration is detected by a pressure sensor monitoring pressure changes in the body indicative of respiration. In another example, respiration is detected by an accelerometer, placed in a manner capable of detecting respiration. In another example, respiration is detected by a heart sound sensor, implanted in the subject 150 or located externally from the subject 150, indicative of respiration. In another example, respiration is detected by an acoustic sensor monitoring respiratory sounds indicative of respiration. In another example, respiration is detected by a position sensor, placed to monitor movement indicative of respiration. In another example, respiration is detected by a thermister located as to monitor temperature changes indicative of respiration, such as outside the nasal openings.

Figure 1B:
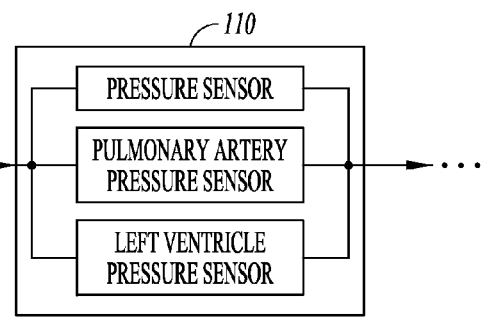
FIG. 1B is a schematic/block diagram illustrating apnea detector components according to one example.

FIG. 1B is a flow chart illustrating generally, by way of example, but not by way of limitation, one example of implementing second apnea detector 110 of apnea classification system 100, such as by using a pressure sensor.

In one example, second apnea detector 110 comprises a pulmonary artery pressure sensor. Recurrent upper airway obstructions, such as those present in obstructive sleep apnea, typically disrupt the stable systemic and pulmonary arterial pressures during sleep with normal breathing. Therefore, by extracting pulmonary artery pressure measurements from a pulmonary artery pressure sensor and conditioning the signal, obstructive sleep apnea can be detected.

In one example, a pulmonary artery pressure signal is extracted from a pulmonary artery pressure sensor. The signal is then filtered, e.g., by computing a moving average over a number of cardiac cycles. Other means, such as zero-cross threshold detection, differentiation, and peak detection, can then be used to analyze the signal and detect signature variations in the pulmonary artery pressure. A period of elevated average pulmonary artery pressure over multiple cycles may be indicative of obstructive sleep apnea.

In another example, second apnea detector 110 comprises a left ventricle pressure sensor. Obstructed inspirations, such as are present in obstructive sleep apnea, typically cause transient, but substantial, increases in left ventricle afterload. Left ventricle afterload typically denotes the pressure the left ventricle has to generate in order to eject blood. FIG. 2 shows that left ventricle end diastolic pressure (LVEDP) drops from 3 mmHg before the obstruction, to −15 mmHg during the obstruction. Therefore, by extracting left ventricle pressure measurements from a left ventricle pressure sensor and conditioning the signal to obtain LVEDP, obstructive sleep apnea can be detected.

Figure 1C:
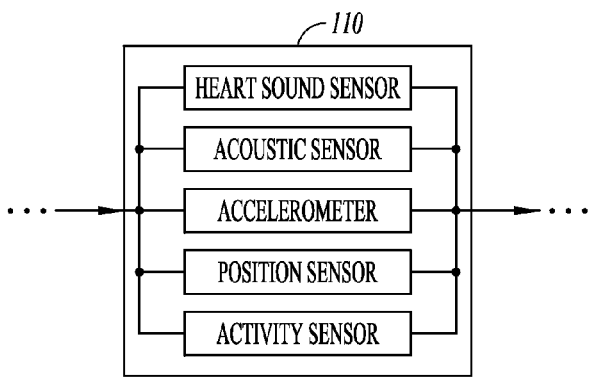
FIG. 1C is a schematic/block diagram illustrating apnea detector components according to one example.

FIG. 1C is a flow chart illustrating generally, by way of example, but not by way of limitation, one example of implementing second apnea detector 110 of apnea classification system 100, such as by using a heart sound sensor.

Figure 3:
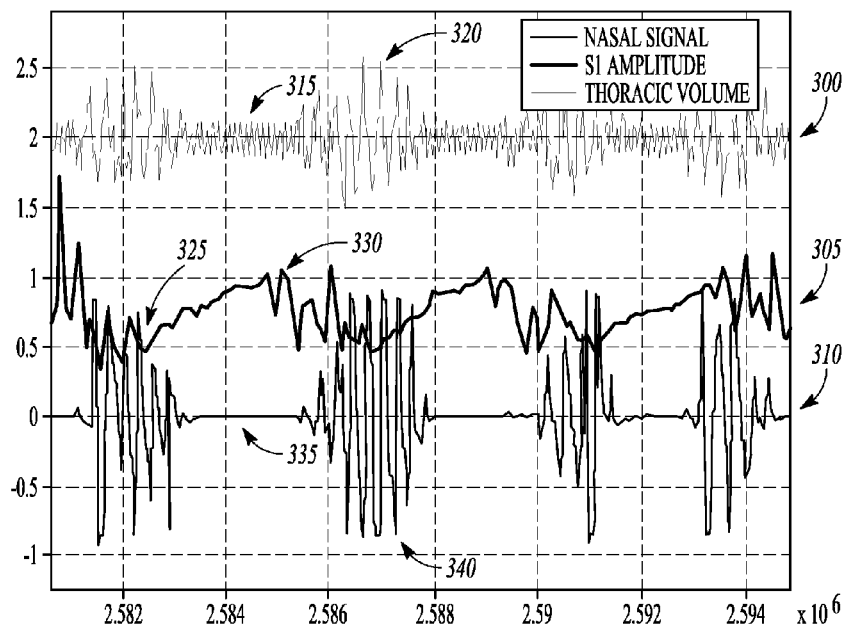
FIG. 3 is a graphical illustration of thoracic volume, S1 amplitude, and nasal signal during a series of inspiratory efforts against a closed airway.

In one example, second apnea detector 110 comprises a heart sound sensor. The normal first heart sound, S1, typically arises as the sound from the mitral valve closure followed by the tricuspid valve closure. Increased ventricular pressure typically increases the intensity of S1, as illustrated in FIG. 3. Lung volume typically changes during respiration. This change causes the volume of blood entering the heart to change. Thus, due to this normal "preload" change, the S1 intensity changes with the increase in blood entering the heart. Because obstructed inspirations cause transient, but substantial, increases in left ventricle afterload, S1 intensity and modulation can be used to detect obstructive sleep apnea.

FIG. 2 is a graphical illustration of a tracheal pressure signal 200 and a left ventricular pressure signal 205 during a series of inspiratory efforts against a closed airway. Inspiratory efforts in tracheal pressure signal 200 are easily identified as the periods in which the tracheal pressure signal 200 goes from positive, at 230, to negative, at 235. A second inspiratory effort is visible as the tracheal pressure signal 200 goes from positive, at 240, to negative, at 245. The pressure spikes in the left ventricle pressure signal 205 are typically indicative of heart muscle contractions. Inspiratory efforts in the left ventricle pressure signal 205 are identified as the periods in which the diastolic baseline of the left ventricle pressure signal 205 goes from positive, 3 mmHg at 210, to negative, −15 mmHg at 215. A second inspiratory efforts is visible as the diastolic baseline of the left ventricle pressure signal 205 goes from positive, 3 mmHg at 220, to negative, −15 mmHg at 225. Thus, the left ventricle pressure signal 205 may be indicative of obstructed sleep apnea.

FIG. 3 is a graphical illustration of a thoracic volume signal 300, S1 amplitude signal 305, and a nasal signal 310 during a series of inspiratory efforts against a closed airway. Each sinusoidal fluctuation in the nasal signal 310 is typically indicative of an individual respiration. Periods of closed airway typically are identified as those where nasal signal 310 is zero, e.g., 335. Periods of breathing typically are identified where nasal signal 310 is not zero, e.g., 340. During zero nasal flow, e.g., 335, S1 amplitude increases, e.g., from 325 to 330. This increase typically occurs over a time period that would correspond to several respiratory cycles, if such breathing were occurring. Thus, such an increase in the S1 amplitude signal 305 may be indicative of obstructed sleep apnea.

Periods of breathing may be identified in the thoracic volume signal 300, e.g., 320. However, periods of closed airway, typically identified as periods of zero nasal flow, e.g., 335, may be non-zero in the thoracic volume signal 300, e.g., 315. This non-zero reading in the thoracic volume signal 300 is typically due to changes in thoracic volume as the subject attempts to breathe. Thus, in some instances, a heart sound sensor will detect obstructive sleep apnea where some respiration sensors, e.g., a thoracic volume sensor, do not.

Figure 4A:
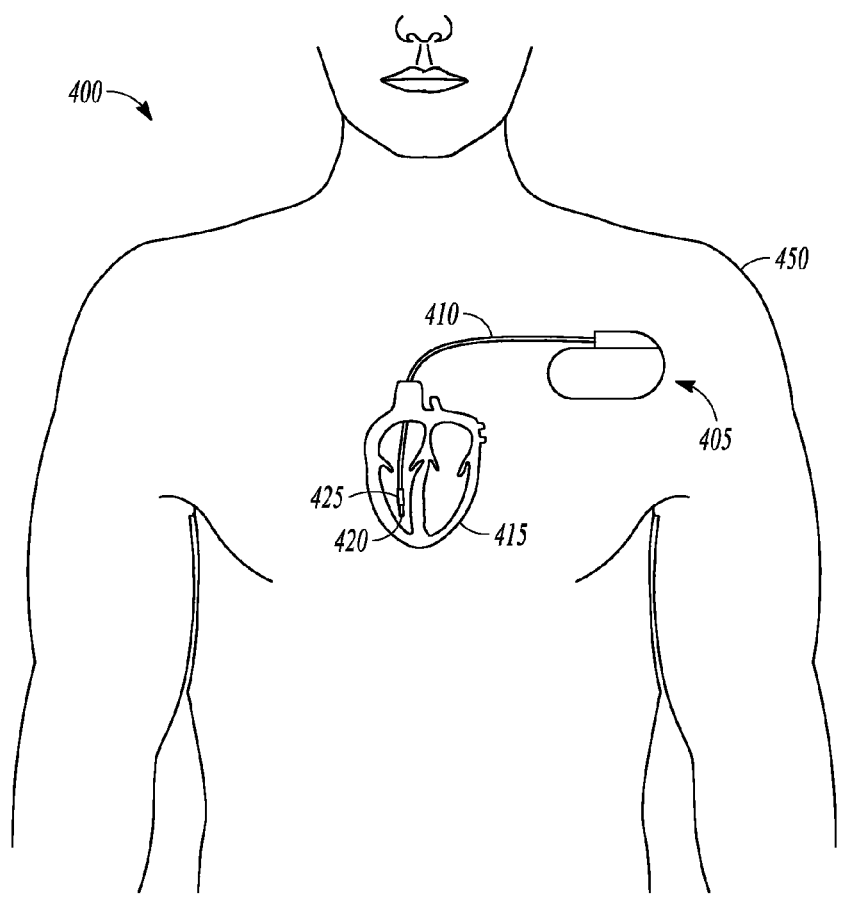
FIG. 4A is a schematic/block diagram illustrating impedance sensor components according to one example.
Figure 4B:
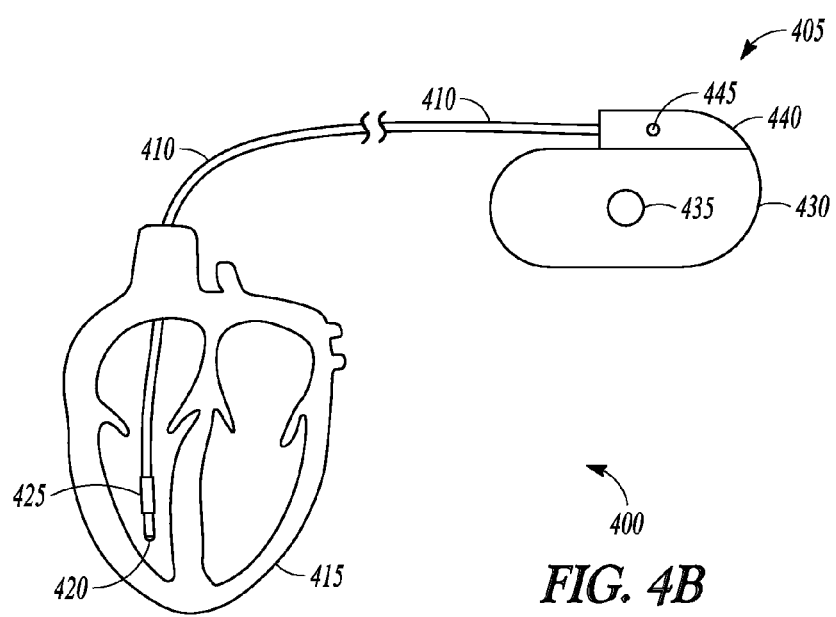
FIG. 4B is a schematic/block diagram illustrating impedance sensor components according to one example.

FIG. 4A and FIG. 4B are schematic/block diagrams illustrating generally, by way of example, but not by way of limitation, one example of implementing first apnea detector 105 by using an impedance sensor system 400. In this example, system 400 includes, among other things, a cardiac rhythm management device 405 and leadwire ("lead") 410 with tip electrode 420 and ring electrode 425 for communicating signals between device 405 and a portion of the subject 450, such as heart 415. Examples of device 405 include bradycardia and antitachycardia pacemakers, cardioverters, defibrillators, combination pacemaker/defibrillators, drug delivery devices, and any other cardiac rhythm management apparatus capable of providing therapy to heart 415.

In one example, system 400 is a transthoracic impedance sensor, such as described in Hartley et al. U.S. Pat. No. 6,076, 015 entitled "RATE ADAPTIVE CARDIAC RHYTHM MANAGEMENT DEVICE USING TRANSTHROACIC IMPEDANCE," assigned to Cardiac Pacemakers, Inc., the disclosure of which is incorporated herein by reference. Other impedance or other detectors may also be used for sensing respiration.

In one example, a first conductor of multiconductor lead 410 electronically couples a first electrode, such as tip electrode 420 (e.g., disposed at the apex of the right ventricle of heart 415), to device 405. A second conductor of multiconductor lead 410 independently electrically couples a second electrode, such as ring electrode 425, to device 405. In one example, device 405 includes a hermetically sealed housing 430, formed from a conductive metal, such as titanium. Housing 430 (also referred to as a "case" or "can") is substantially covered over its entire surface by a suitable insulator, such as silicone rubber, except for at a window that forms a third electrode, referred to as a "case" or "can" electrode 435. In one embodiment, a header 440 is mounted on housing 430 for receiving lead 410. Header 440 is formed of an insulative material, such as molded plastic. Header 440 also includes at least one receptacle, such as for receiving lead 410 and electrically coupling conductors of lead 410 to device 405. Header 440 can also include a fourth electrode, referred to as indifferent electrode 445.

In one example, an excitation signal, such as a strobed sequence of current pulses or other measurement stimuli, to heart 415 (e.g., between ring electrode 425 and tip electrode 420, or using any other electrode configuration suitable for such excitation). In response to the excitation signal, a response signal is sensed in the cardiac rhythm management device 405 (e.g., between tip electrode 420 and indifferent electrode 445, or any other suitable electrode configuration).

In one example, the response signal sensed by the cardiac rhythm management device 405 is a voltage that represents transthoracic (i.e., across a portion of the chest or thorax) impedance, which includes respiration information.

Figure 5:
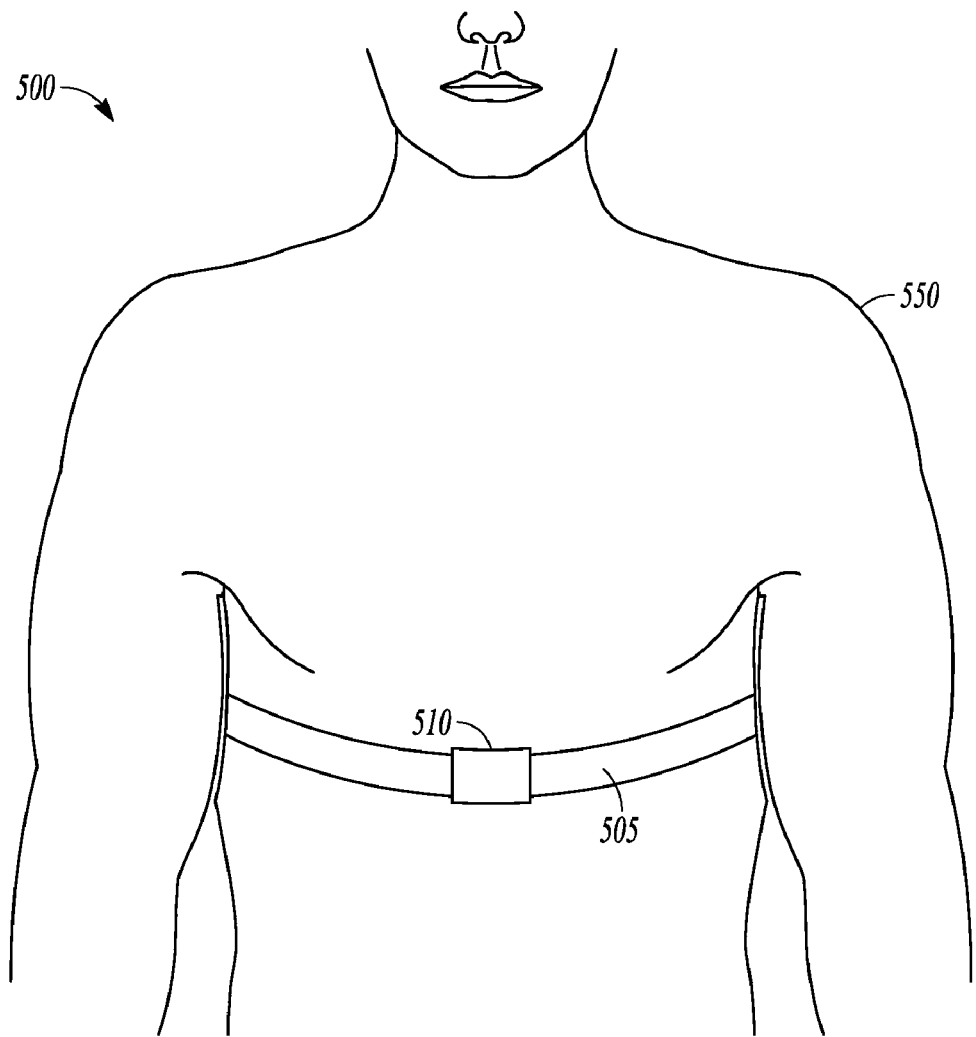
FIG. 5 is a schematic/block diagram illustrating position sensor components according to one example.

FIG. 5 is a schematic/block diagram illustrating generally, by way of example, but not by way of limitation, one example of implementing first apnea detector 105 by using a position sensor system 500 according to the present invention. System 500 includes a band 505 placed around the abdomen or thorax, and a sensor 510 to monitor position changes of the band.

In one example, the system 500 includes a band 505 located around the thorax to measure chest wall movement, and position sensor 510 that detects and records the movement. Band 505 may be any material capable of being located around the abdomen or thorax. Band 505 may be placed in any location capable of sensing movement correlated to respiration. Other position sensors may also be used for sensing respiration.

Figure 6:
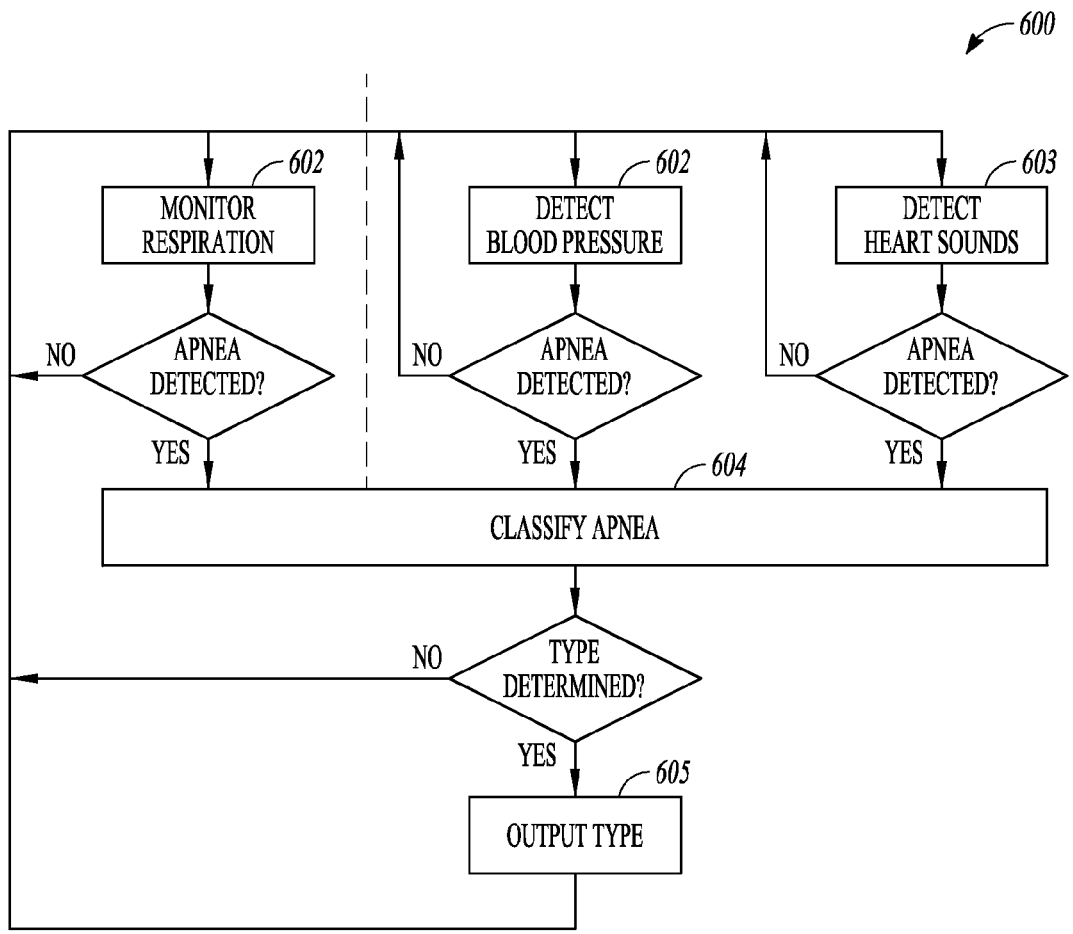
FIG. 6 is a flow chart according to one example.

FIG. 6 is a flow chart illustrating generally, by way of example, but not by way of limitation, one example of implementing an apnea classification method 600. At 601, first apnea detector 105 is monitoring the respiration of subject 150. In one example, the monitoring begins as system 100 is activated. In another example, the monitoring begins in response to a user command. In another example, the monitoring begins at a predetermined time or upon a predetermined triggering event. In one example, the monitoring lasts for a predetermined duration after it begins. In another example, the monitoring lasts for as long as system 100 is active. In another example, the monitoring begins on a recurring basis and may last for a specified duration.

At 602, second apnea detector 110 is detecting the blood pressure of subject 150. In one example, the detection begins as system 100 is activated. In another example, the detection begins in response to a user command. In another embodiment, the detection begins at a predetermined time or upon a predetermined triggering event. In one example, the detection lasts for a predetermined duration after it begins. In another example, the detection lasts for as long as system 100 is active. In another example, the detection begins on a recurring basis and may last for a specified duration.

At 603, second apnea detector 110 is detecting heart sounds of subject 150. In one example, the detection begins as system 100 is activated. In another example, the detection begins in response to a user command. In another embodiment, the detection begins at a predetermined time or upon a predetermined triggering event. In one example, the detection lasts for a predetermined duration after it begins. In another example, the detection lasts for as long as system 100 is active. In another example, the detection begins on a recurring basis and may last for a specified duration.

At 604, apnea classifier module 115 classifies apnea from information received from first apnea detector 105 and second apnea detector 110. At 605, apnea classification system output 120 displays the type of apnea determined at apnea classifier module 115.

In one example, at 604, apnea classifier module 115 receives data from first apnea detector 105 when an apnea event is detected. In another example, apnea classifier module 115 receives data from first apnea detector 105 when an apnea event is not detected. In one example, first apnea detector 105 continues monitoring subject 150 following the detection of an apnea event. In another example, first apnea detector 105 ceases monitoring subject 150 following the detection of an apnea event.

In another example, at 604, apnea classifier module 115 receives data from second apnea detector 110 when an apnea event is detected. In another example, apnea classifier module 115 receives data from second apnea detector 110 when an apnea event is not detected. In one example, second apnea detector 110 continues monitoring subject 150 following the detection of an apnea event. In another example, second apnea detector 110 ceases monitoring subject 150 following the detection of an apnea event.

At 604, apnea is classified from information received from monitoring respiration, 601, and at least one of detecting blood pressure, 602, and detecting heart sounds, 603. In one example, if the apnea type is distinguished, the result is stored within the apnea classifier module 115 or apnea classification system output 120 for later utilization. In another example, if the apnea type is distinguished, the result is used to begin therapy specific to the type of apnea present. In another example, if the apnea type is distinguished, the result is communicated to a third person, such as a doctor. In another example, if the apnea type is distinguished, the result is sent external to the apnea classification system 100. In another example, if the apnea type is distinguished, the result is utilized in a manner comprising at least one of being stored within the apnea classifier module 115 or apnea classification system output 120 for later utilization, being used to begin therapy specific to the type of apnea present, being communicated to a third person, being sent external to the apnea classification system 100.

In one example, at 604, if information is received that apnea is detected from monitoring respiration, 601, and information is received that apnea is detected from at least one of detecting blood pressure, 602, and detecting heart sounds, 603, type obstructiveسلeep apnea has been determined. In another example, at 604, if information is received that apnea is detected from monitoring respiration, 601, and information is received that apnea is not detected from detecting blood pressure, 602, or detecting heart sounds, 603, type central sleep apnea has been determined. In another example, at 604, if information is received that apnea is not detected from monitoring respiration, 601, and information is received that apnea is detected from at least one of detecting blood pressure, 602, and detecting heart sounds, 603, type obstructive sleep apnea has been determined. In another example, at 604, if information received from monitoring respiration, 601, detecting blood pressure, 602, and detecting heart sounds, 603, is conflicting, no apnea type has been determined, and system 100 continues to monitor for an apnea event.

In one example, at 604, apnea is classified according to Table 1.

TABLE 1

| | Monitor Respiration | Detect Blood Pressure/Heart Sounds | Apnea Type Determined |
|---|---|---|---|
| Apnea Detected? | Yes | Yes | Obstructed Sleep Apnea |
| Apnea Detected? | Yes | No | Central Sleep Apnea |
| Apnea Detected? | No | Yes | Obstructed Sleep Apnea |
| Apnea Detected? | No | No | None |

In one example, at 604, if the apnea type is not distinguished, the information is discarded and apnea classifier module 115 continues to monitor information from first apnea detector 105 and second apnea detector 110. In another example, at 604, if the apnea type is not distinguished, the data is stored and apnea classifier module 115 continues to monitor information from first apnea detector 105 and second apnea detector 110. In another example, at 604, if the apnea type is not distinguished, the data is sent external to the apnea classification system 100.

Other Examples

In an example, the apnea classification system 100 can be used to distinguish between respiration types, such as sleep apnea (e.g., OSA or CSA) or hypopnea, using information from a respiration-based apnea detector and a non-respiration-based apnea detector. In an example, the apnea classification system 100 can be configured to identify a duration of periodic respiration, where the duration of periodic respiration can include a duration of sleep apnea, such as during Cheyne-Stokes respiration, or a duration of hypopnea. In an example, a therapy can be enabled or inhibited using information about the distinguished respiration type.

Figure 7:
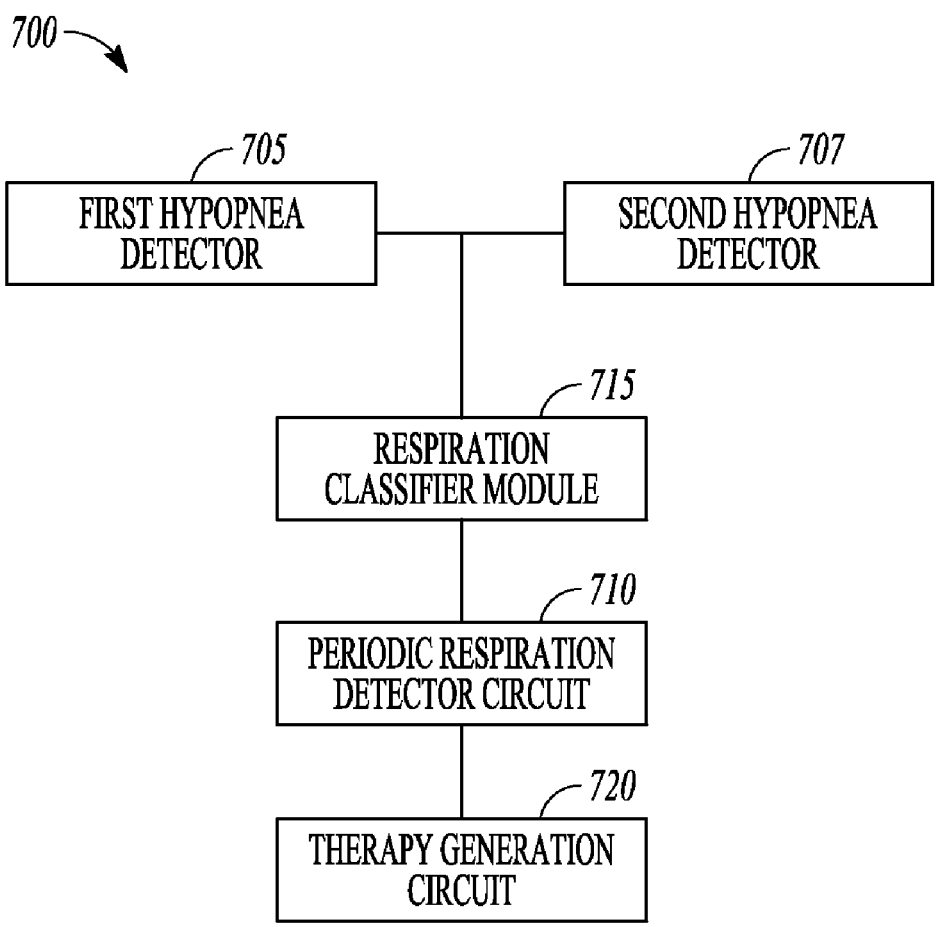
FIG. 7 illustrates generally a portion of a system for identifying a respiration type and enabling or inhibiting a therapy using the identified respiration type.

FIG. 7 illustrates generally a portion of a system 700 that can be configured for identifying a respiration type and for enabling or inhibiting a response, such as a therapy, using the identified respiration type. The system 700 can include the first implantable or external apnea detector 105, the second implantable or external apnea detector 110, the apnea classifier module 115, a first implantable or external hypopnea detector 705, a second implantable or external hypopnea detector 707, a respiration classifier module 715, a periodic respiration detector circuit 710, and a response generation circuit such as a therapy generation circuit 720. In an example, at least a portion of the system 700 can be configured to be located within an implantable medical device (IMD), such as the cardiac rhythm management device 405, or at least a portion of the system 100 can be configured to be located external to the IMD.

As discussed above with respect to FIG. 1, and FIGS. 1A-1C, the first apnea detector 105 can be respiration-based, such as to detect a degree to which the subject is breathing. In an example, the first apnea detector 105 can optionally be configured as the hypopnea detector 705 such as to distinguish hypopnea. Similarly, the second apnea detector 110 can include one or more non-respiration-based sensors that can be configured to sense a parameter indicative of apnea other than whether the subject is breathing and that can be optionally configured as the second hypopnea detector 707 such as to detect hypopnea. The apnea classifier module 115 can optionally be configured to be a respiration classifier module 715. The respiration classifier module 715 can be configured to receive information from the first apnea detector 105, the second apnea detector 110, the first hypopnea detector 705, and the second hypopnea detector 707 and to use such received information to provide a respiration classification, such as sleep apnea (e.g., OSA or CSA,) hypopnea, or hyperpnea.

In an example, the apnea classifier module 115 can be configured to identify a variation to the subject's respiration cycles, such as including an event associated with diminished respiration such as sleep apnea or hypopnea. Hypopnea differs from sleep apnea. During hypopnea, some air flow remains. Hypopnea can be characterized by a period of shallow breathing, abnormally slow respiration, or both. Like sleep apnea, hypopnea can be classified as central or obstructive. However, during obstructive hypopnea, the airway remains partially open. The reduced respiration during hypopnea can cause oxygen desaturation of the blood and can interrupt the sleep period of the subject. In an example, hypopnea can be characterized as a short duration decrease in respiration from normal airflow to an airflow that is between about 25% and about 70% of the normal airflow.

In an example, the first hypopnea detector 705 can detect an indication of hypopnea by detecting a reduction in respiration, such as a reduction in respiration amplitude or a reduction in respiration rate, from the respective normal respiration amplitude or normal respiration rate of the subject. In an example, during an identified period of hypopnea, the respiration amplitude, respiration rate, or both can be reduced to be within a specified range, such as to between about 25% to about 70% of the subject's normal respiration amplitude or normal respiration rate, respectively.

In an example, the second hypopnea detector 707 can include an oxygen saturation sensor that can be used to determine a non-respiration indicator of hypopnea. As described above, the second apnea detector 110 can be used to identify a non respiration indicator of apnea, such as a gradual change to LVEDP over several respiratory cycles or a gradual rise in S1 heart sound amplitude during obstructed breathing. During hypopnea, however, the amplitude of such signals remains substantially unchanged from the amplitude value taken during normal respiration. For example, a non-respiration indicator of hypopnea can include a reduction in the subject's blood oxygen saturation level (e.g., a decrease of about four percent or more) due to the diminished airflow, during hypopnea, over a time period corresponding to several respiratory cycles. Although changes to a blood oxygen saturation level can be affected by respiration, the reduction in blood oxygen saturation level does not manifest cyclic information corresponding to inhaling and exhaling cycles, it is not considered to be a respiration sensor within the meaning of this document.

The respiration classifier module 715 can be configured to distinguish hypopnea from other respiration disturbances using information, from the first hypopnea detector 705, such as an indication of reduced respiration to within a range between about 25% and 70% of the subject's normal respiration amplitude and information, from the second hypopnea detector 707, such as a reduction to the subject's blood oxygen level by at least 4%.

In an example, the system 100 can include the periodic respiration detector circuit 710. In an example, the periodic respiration detection circuit 710 can be configured to receive data from the first apnea detector 105, the second apnea detector module 110, the first hypopnea detector 705, the second hypopnea detector 707, and the apnea classification circuit 115. For example, the periodic respiration detection circuit can be configured to distinguish Cheyne-Stokes respiration from periodic respiration. Cheyne Stokes respiration, such as at 840 of FIG. 8, can be identified by two or more periods of sleep apnea (e.g., greater than about three seconds), with consecutive periods of sleep apnea separated by one or more periods of hyperpnea (e.g., less than about twenty seconds.) Periodic respiration can include two or more periods of hypopnea (e.g., greater than about three seconds), with consecutive periods of hypopnea separated by one or more periods of normal or fast respiration (e.g., hyperpnea or normal respiration), such as of less than about twenty seconds.

In an example, the system 100 can include the therapy generation circuit 720. The therapy generation circuit 720 can include a neural stimulation device, such as to provide, withhold, or inhibit an electrical, mechanical, optical, acoustic, or chemical stimulation to one or more neural targets. The therapy generation circuit 720 can be configured to generate an electrostimulation, such as one or more of a phrenic nerve stimulation therapy or a hypoglossal nerve stimulation therapy. For example, the therapy generation circuit 710 can be configured to generate an electrostimulation that can be delivered to one or more of a variety of nerve sites (e.g., a hypoglossal nerve site, a phrenic nerve site, a vagal nerve site, etc.), such as to activate a non-cardiac muscle (e.g., the genioglossus muscle, the diaphragm, etc.) In an example, the therapy generation circuit 710 can be configured to generate a non-neural electrostimulation therapy, such as a cardiac pacing, cardiac resynchronization, or other cardiac rhythm management therapy.

The therapy generation circuit 720 can be configured to adjust automatically one or more of an electrostimulation pulse width, an electrostimulation pulse amplitude, or a timing of delivery of electrostimulation therapy. For example, the electrostimulation pulse width or electrostimulation pulse amplitude can be adjusted such that the duty cycle of the electrostimulation therapy remains within a range between about 35% to about 50% to avoid causing fatigue to the stimulated nerve or muscle. In an example to reduce muscle fatigue or nerve fatigue, the therapy generation circuit can adjust the delivery of the electrostimulation therapy such that the electrostimulation energy is delivered over only a portion of a breath. For example, an electrostimulation therapy can be generated for each breath, or over a duration of several breaths. For example, a phrenic nerve stimulation therapy, or a hypoglossal nerve stimulation therapy, can be generated, in response to a detected sleep apnea event, such that the electrostimulation energy can be generated over a duration between about the start of a breath to about the end of the breath.

Figure 8:
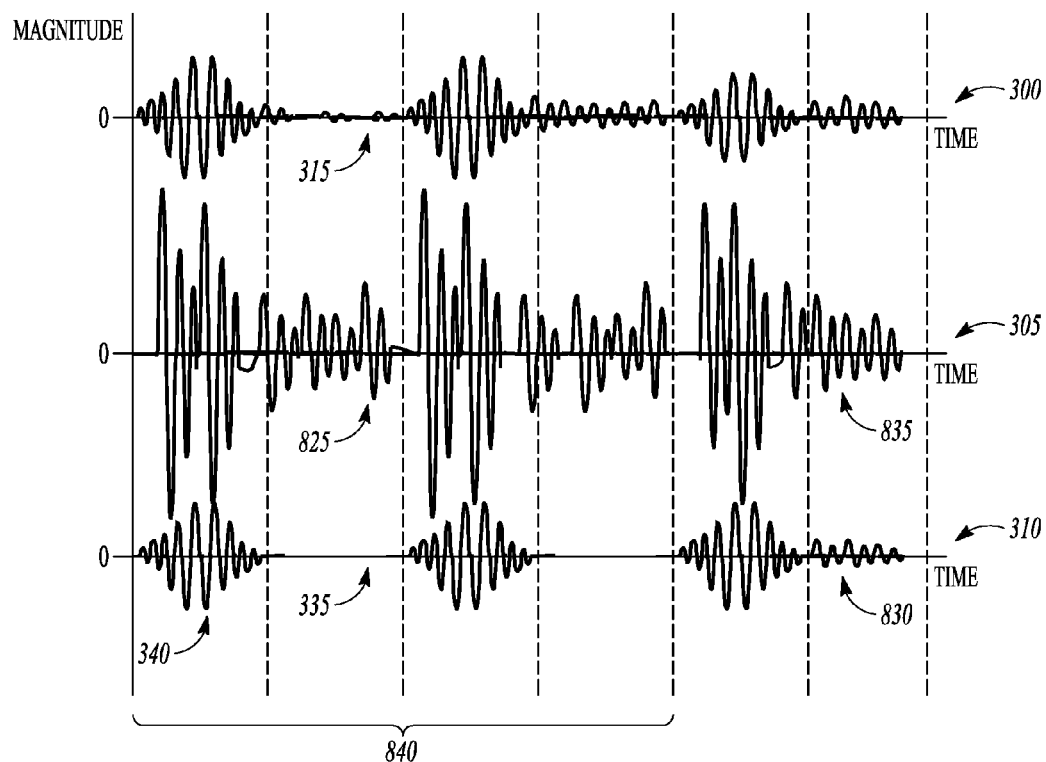
FIG. 8 illustrates generally an example of a relationship between thoracic volume, S1 amplitude, and nasal signal over a duration.

FIG. 8 illustrates generally an example of a relationship between the thoracic volume 300, the S1 amplitude signal 305, and the nasal (airflow) signal 310 over a duration of respiration. As described above with respect to FIG. 3, each sinusoidal fluctuation in the nasal signal 310 can be indicative of an individual respiration (a breathing cycle). Durations of respiration can be identified as those where the nasal signal 310 is non-zero, such as at 340 or 830. A duration of no respiration can be identified where the nasal signal 310 is zero, such as at 335. In an example, a duration of diminished respiration (e.g., hypopnea) 830 can be identified where the respiration signal amplitude (e.g., at the peak magnitude or at an average of a series of peak magnitudes) is less than the respiration signal amplitude during normal respiration over the duration of hypopnea 830, such as by at least a specified threshold value.

During a duration of sleep apnea 335 or a duration of hypopnea 830, the S1 amplitude may remain substantially stable (e.g., at 825 or at 835). During central sleep apnea, respiration can cease without the signs of inspiratory efforts against a closed airway, as discussed above with respect to FIG. 3 with obstructive sleep apnea. For example, a duration of central sleep apnea can be associated with a duration of zero respiration 335 corresponding to a duration of S1 amplitude 305 that does not increase, such as at 825, and where the thoracic volume signal 300 is about zero, such as at 850. A duration of Cheyne-Stokes respiration 840 can be identified as at least two consecutive durations of hyperpnea 330 that are separated by a time period that includes a duration of sleep apnea 335. Periodic respiration can be identified as at least two consecutive durations of hypopnea 830 that are separated by a time period that includes a duration of hyperpnea 330.

Figure 9:
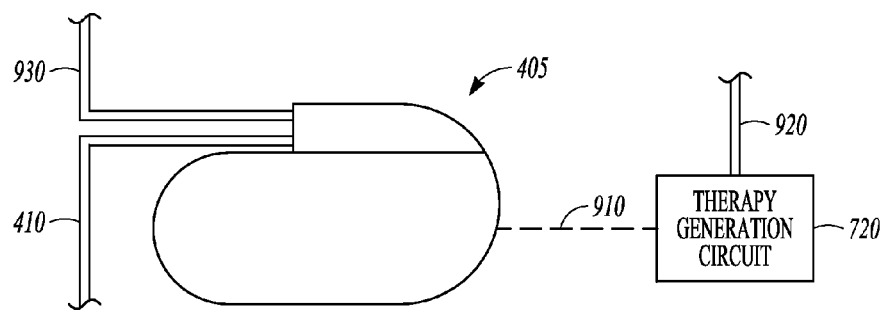
FIG. 9 illustrates generally a portion of a system for enabling or inhibiting a therapy using an identified respiration type.

FIG. 9 illustrates generally a portion of a system that can be configured for using an identified respiration type for enabling or inhibiting a therapy. System 900 can include a cardiac rhythm management device 405, such as discussed with respect to FIG. 4, which can be coupled to a lead wire 410, a neural stimulation lead wire 930, or both. The system 900 can include a therapy generation circuit 720 and a neural stimulation lead 920. The therapy generation circuit 720 can be communicatively coupled to the cardiac rhythm management device 405 via a communicative coupling 910, such as using radio frequency (RF) signals or other telemetry capabilities. The external therapy generation circuit 720 can be implantable within the subject, or located external to the subject. The therapy generator circuit 720 can be implanted or optionally anchored in a subcutaneous pocket, in the neck of the subject, or subcutaneously near the cranium, such as behind the ear. In an example, the cardiac rhythm management device 405 can include the therapy generation circuit 720 within its hermetically-sealed enclosure. In an example, the neural stimulation leads 920 can be configured to be coupled via an electrode to one or more nerve sites, such as located on the phrenic nerve or the hypoglossal nerve. An example of hypoglossal nerve stimulation therapy is discussed in the U.S. Pat. No. 7,809,442 entitled "Obstructive Sleep Apnea Treatment Devices, Systems, and Methods, in which sites located on or near the hypoglossal nerve are stimulated to increase the patency of the airway of the subject during an obstructive sleep apnea event. An example of a therapy using phrenic nerve therapy is discussed in U.S. Pat. No. 7,340,302 to Falkenberg, et al., entitled "Treating Sleep Apnea in Patents Using Phrenic Nerve Stimulation," in which the phrenic nerve is stimulated to "awaken" the respiration system and minimize episodes of sleep apnea.

Figure 10:
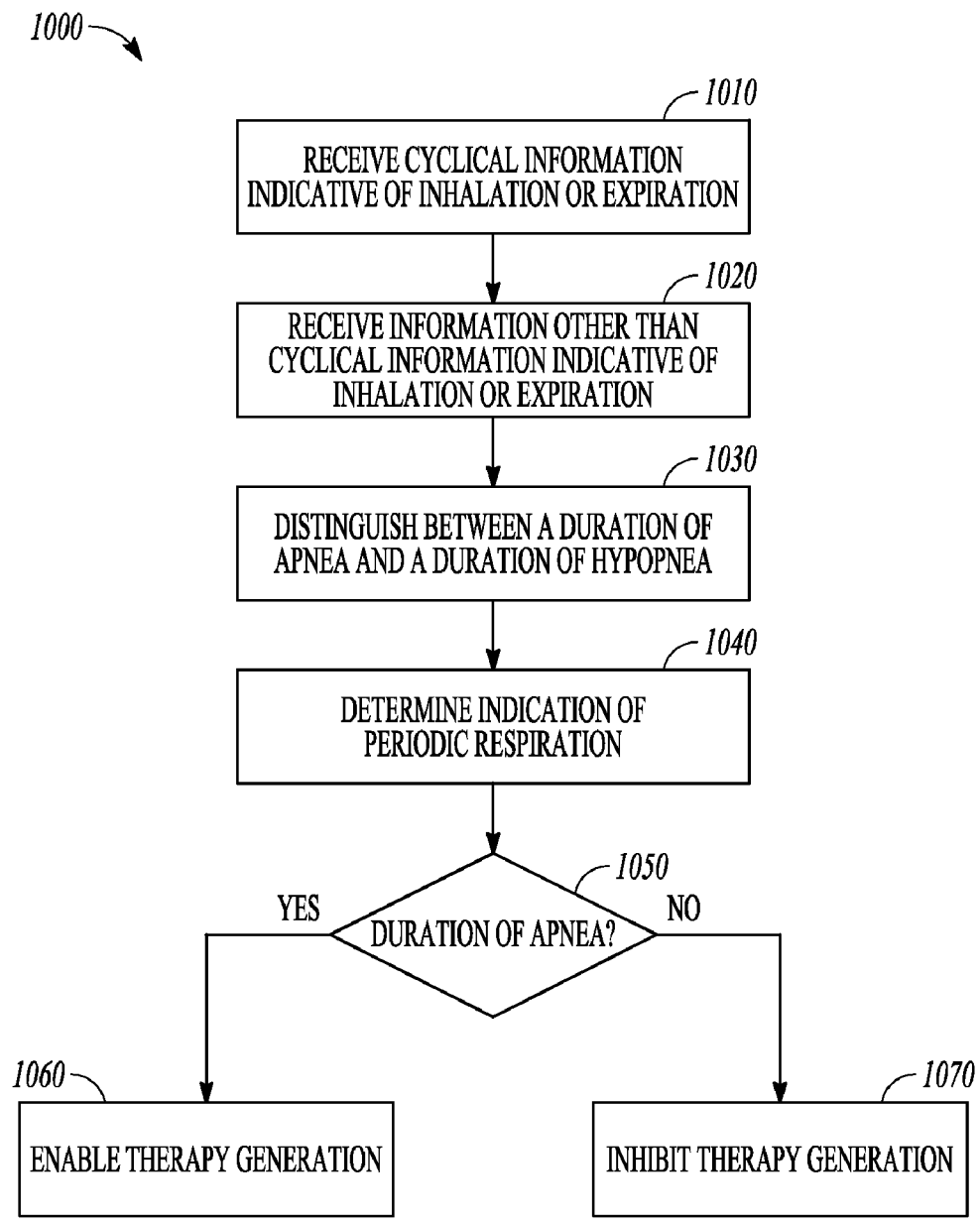
FIG. 10 illustrates generally an example of a portion of a method such as including identifying a respiration type over a duration and enabling or inhibiting a therapy using the identified respiration type.

FIG. 10 illustrates generally an example of a technique 1000 such as for identifying a respiration type over a duration and enabling or inhibiting a therapy using the identified respiration type, such as included in the system of one or more of FIG. 1, 4, 7 or 9. At 1010, the first apnea detector 105 or the first hypopnea detector 705 can be configured to receive cyclical information indicative of the respiration of the subject 150. At 1020, the second apnea detector 110 or the second hypopnea detector 707 can be configured to receive information other than such cyclical information indicative of inhalation or expiration of the subject 150, such as a blood oxygen saturation signal, a heart sound signal or a thoracic volume signal.

At 1030, the apnea classifier module 115 can receive information from the first apnea detector 105 and the second apnea detector 110 and can classify the respiration as an apnea, as described above with FIG. 3. The respiration classification module 715 can receive information from the first hypopnea detector 705, and the second hypopnea detector 707 and can distinguish the respiration as hypopnea using the information. For example, the respiration classification module 715 can classify the respiration as hypopnea when the first hypopnea detector 705 indicates hypopnea as a drop in respiration amplitude between 25% and 70% of normal and the second hypopnea detector 707 indicates hypopnea such as when the blood oxygen saturation level drops to a level about 4% of normal. The apnea classification system output 120 can be configured to display whether apnea was determined by the apnea classifier module 115 or hypopnea was determined by the respiration classification module 715.

At 1040, the periodic respiration detector circuit 710 can receive information from the first apnea detector 105, the second apnea detector 110, the apnea classifier module 115, the first hypopnea detector 705, the second hypopnea detector 707, or the respiration classifier module 715. The periodic respiration detector circuit 710 can identify a duration of Cheyne-Stokes respiration by identifying at least two durations of sleep apnea adjacent to a duration of respiration, such as hypopnea or normal respiration. For example, a duration of Cheyne-Stokes respiration can be identified when the periodic respiration detector circuit 710 identifies at least two durations of sleep apnea greater than a specified duration (e.g., 3 seconds) adjacent to at least two durations of hyperpnea of a duration less than a specified duration (e.g., 20 seconds.) For example, a duration of periodic respiration can be identified when the periodic respiration detector circuit 710 identifies at least two durations of hypopnea greater than a specified duration (e.g., 3 seconds) adjacent to at least two durations of hyperpnea of a duration less than a specified duration (e.g., 20 seconds.)

At 1050, the therapy generation circuit 720 can be configured to receive information about a duration of an identified respiration type, including sleep apnea (e.g., central sleep apnea, or obstructive sleep apnea), hypopnea, hyperpnea, or normal respiration from the apnea classification circuit 115, or the respiration classification circuit 715. In an example, the therapy generation circuit 720 can be configured to use the identified respiration type to enable or inhibit the generation of a therapy. If a duration of sleep apnea was identified at 1050, then the therapy generation circuit 720 can enable an electrostimulation therapy at 1060. For example, the therapy generation circuit 720 can be configured to enable a hypoglossal nerve electrostimulation therapy during a duration of identified obstructive sleep apnea, or enable a phrenic nerve electrostimulation therapy during a duration of identified central sleep apnea. The therapy can be enabled after the start of an apnea (e.g., after the duration of a respiration cycle) and to end prior to the end of the detected duration of apnea.

Returning to 1050, if a duration of sleep apnea was not identified, then the therapy generation circuit 720 can inhibit the electrostimulation therapy at 1070. In an example, the therapy generation circuit 720 can inhibit the generation of an electrostimulation therapy during an identified duration of hypopnea, hyperpnea, or normal respiration.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
a respiration-based apnea detector configured to receive cyclic information indicative of inhalation or exhalation;
a non-respiration-based apnea detector configured to receive information other than cyclic information indicative of inhalation or exhalation; and
an apnea classifier module, coupled to the respiration-based and non-respiration-based apnea detectors, configured to distinguish between sleep apnea and hypopnea using information from both the respiration-based and non-respiration-based apnea detectors.

2. The system of claim 1, wherein the respiration-based apnea detector includes a respiration sensor configured to sense cyclic information indicative of inhalation or exhalation.

3. The system of claim 2, wherein the respiration sensor includes at least one of an impedance sensor configured to detect impedance information or a blood pressure sensor configured to detect blood pressure information; and
wherein the respiration-based apnea detector is configured to receive the cyclic information indicative of inhalation or exhalation from at least one of the impedance information or the blood pressure information.

4. The system of claim 3, wherein the blood pressure sensor is configured to sense a left ventricle end diastolic pressure (LVEDP); and
wherein the apnea classifier module is configured to distinguish between apnea and hyperpnea using an increase in magnitude of a sensed LVEDP during a detected apnea.

5. The system of claim 1, wherein the non-respiration-based second apnea detector includes a blood pressure sensor configured to be located in association with a ventricle and to measure a ventricular pressure; and
wherein the apnea classifier module is configured to distinguish between apnea and hyperpnea using respiration information from the first respiration-based first apnea detector and ventricular pressure information from the non-respiration-based second apnea detector.

6. The system of claim 1, wherein the apnea classifier module is further configured to distinguish between Obstructive Sleep Apnea (OSA) and central sleep apnea (CSA) using the information from both the respiration-based and non-respiration-based apnea detectors.

7. The system of claim 1, comprising a periodic respiration detector circuit configured to identify periodic respiration using the information from both the respiration-based and non-respiration-based apnea detectors, and the sleep apnea indication or the hypopnea indication, wherein the periodic respiration comprises a duration of normal or increased respiration and a subsequent duration of diminished respiration.

8. The system of claim 7, wherein the periodic respiration detector circuit is configured to identify Cheyne-Stokes respiration using information from both the respiration-based and non-respiration-based apnea detectors.

9. The system of claim 7, wherein the periodic respiration comprises a first duration of hyperpnea and a second duration of hypopnea.

10. The system of claim 1, comprising a therapy generation circuit configured to enable therapy during a duration of sleep apnea or inhibit therapy generation during a duration of hypopnea.

11. The system of claim 10, wherein the therapy generation circuit is configured to enable phrenic nerve therapy during a duration of central sleep apnea using information from both the respiration-based and non-respiration-based apnea detectors.

12. The system of claim 10, wherein the therapy generation circuit is configured to enable a hypoglossal nerve therapy during a duration of obstructive sleep apnea using information from both the respiration-based and non-respiration-based apnea detectors.

13. A method comprising:
receiving cyclical information indicative of inhalation or expiration;
receiving physiological information indicative of respiration other than cyclical information indicative of inhalation or exhalation; and
distinguishing, using a processor, between sleep apnea and hypopnea using the cyclical information indicative of inhalation or expiration and the information other than cyclical information indicative of inhalation or exhalation.

14. The method of claim 13, including detecting apnea using the cyclical information indicative of inhalation or expiration;
wherein the receiving information other than cyclical information indicative of inhalation or exhalation includes receiving ventricular pressure information from a blood pressure sensor configured to be located in association with a ventricle; and
wherein the distinguishing between OSA and CSA includes using the ventricular pressure information during the detected apnea.

15. The method of claim 14, wherein the receiving ventricular pressure information includes receiving a left ventricle end diastolic pressure (LVEDP); and
wherein the distinguishing between OSA and CSA includes using an increase in magnitude of the LVEDP during the detected apnea.

16. The method of claim 13, comprising identifying periodic respiration using the information from both the respiration-based and non-respiration-based apnea detectors, and the sleep apnea indication or the hypopnea indication, wherein the periodic respiration comprises a duration of normal or increased respiration and a subsequent duration of diminished respiration.

17. The method of claim 13, comprising a enabling therapy during a duration of sleep apnea or inhibiting therapy generation during a duration of hypopnea.

18. The method of claim 13, comprising enabling phrenic nerve therapy during a duration of central sleep apnea using information from both the respiration-based and non-respiration-based apnea detectors.

19. The method of claim 13, comprising enabling hypoglossal nerve therapy during a duration of obstructive sleep apnea using information from both the respiration-based and non-respiration-based apnea detectors.

20. A non-transitory processor-readable medium comprising instructions that, when executed by the processor, cause the processor to:
receive cyclical information indicative of inhalation or expiration;
receive physiological information indicative of respiration other than cyclical information indicative of inhalation or exhalation; and
distinguish between sleep apnea and hypopnea using the cyclical information indicative of inhalation or expiration and the information other than cyclical information indicative of inhalation or exhalation.

* * * * *